United States Patent
Griffin, Jr.

(10) Patent No.: US 6,275,563 B1
(45) Date of Patent: Aug. 14, 2001

(54) PORTABLE GAMMA APPARATUS FOR CORE ANALYSIS AND METHOD THEREFOR

(75) Inventor: Theodore Joseph Griffin, Jr., Spring, TX (US)

(73) Assignee: Core Laboratories, I.P., Inc., Houston, TX (US)

( * ) Notice: Subject to any disclaimer, the term of this patent is extended or adjusted under 35 U.S.C. 154(b) by 0 days.

(21) Appl. No.: 09/228,715

(22) Filed: Jan. 12, 1999

(51) Int. Cl.[7] .................................................. G01B 15/06
(52) U.S. Cl. ............................................... 378/58; 378/59
(58) Field of Search ............. 73/152.11; 256/253–269.8; 378/37, 57, 58, 59, 60

(56) References Cited

U.S. PATENT DOCUMENTS

| | | | |
|---|---|---|---|
| 2,719,926 | * 10/1955 | Procter et al. | 378/59 |
| 3,566,117 | 2/1971 | Tixler | 250/83.1 |
| 3,942,003 | 3/1976 | Apenberg et al. | 250/255 |
| 4,464,930 | 8/1984 | Givens | 73/152 |
| 4,467,642 | 8/1984 | Givens | 73/152 |
| 4,617,825 | 10/1986 | Ruhovets | 73/152 |
| 4,623,792 | * 11/1986 | Bohme et al. | 250/255 |
| 4,794,792 | 1/1989 | Flaum et al. | 73/152 |
| 4,820,919 | 4/1989 | Berg et al. | 250/269 |
| 4,849,627 | 7/1989 | Moake | 250/255 |
| 4,854,163 | 8/1989 | Mount, II et al. | 73/152 |
| 4,909,075 | 3/1990 | Flaum et al. | 73/152 |
| 4,916,616 | 4/1990 | Freedman et al. | 364/422 |
| 4,947,045 | 8/1990 | Birks et al. | 250/360.1 |
| 5,017,778 | 5/1991 | Wraight | 250/254 |
| 5,109,697 | 5/1992 | Millheim et al. | 73/153 |
| 5,165,275 | 11/1992 | Donovan | 73/153 |
| 5,204,529 | 4/1993 | Diatschenko | 250/268 |
| 5,205,167 | 4/1993 | Gartner et al. | 73/155 |
| 5,268,952 | * 12/1993 | Tarvainen | 378/59 |
| 5,357,797 | 10/1994 | Maki, Jr. et al. | 73/152 |
| 5,361,632 | 11/1994 | Magnami | 73/153 |
| 5,388,456 | 2/1995 | Kettel | 73/152 |
| 5,390,115 | 2/1995 | Case et al. | 364/422 |
| 5,506,769 | 4/1996 | Fu et al. | 364/422 |
| 5,571,962 | 11/1996 | Georgi et al. | 73/152.04 |
| 5,627,368 | 5/1997 | Moake | 250/269.3 |
| 5,736,636 | 4/1998 | Mozelev et al. | 73/152.05 |

* cited by examiner

Primary Examiner—David P. Porta
(74) Attorney, Agent, or Firm—Barry S. Newberger; Winstead Sechrest & Minick

(57) ABSTRACT

An apparatus and method for a wellsite γ-ray analysis of core samples is implemented. A wheeled carriage supporting a γ-ray detector stably straddles a core sample, which may be encased in a core barrel. A bracket attached to the carriage may hold a radionuclide source of γ radiation positioned distally from the detector, thereby forming a space therebetween for passage of the core. The density of the core may be determined by counting the γ flux attenuated by the core; by traversing the carriage along a length of the core, the density may be determined as a function of position, and disrupted core or partial recovery detected thereby. Additionally, the natural γ emission of the core may be observed by traversing the apparatus along the core without the radionuclide source.

27 Claims, 5 Drawing Sheets

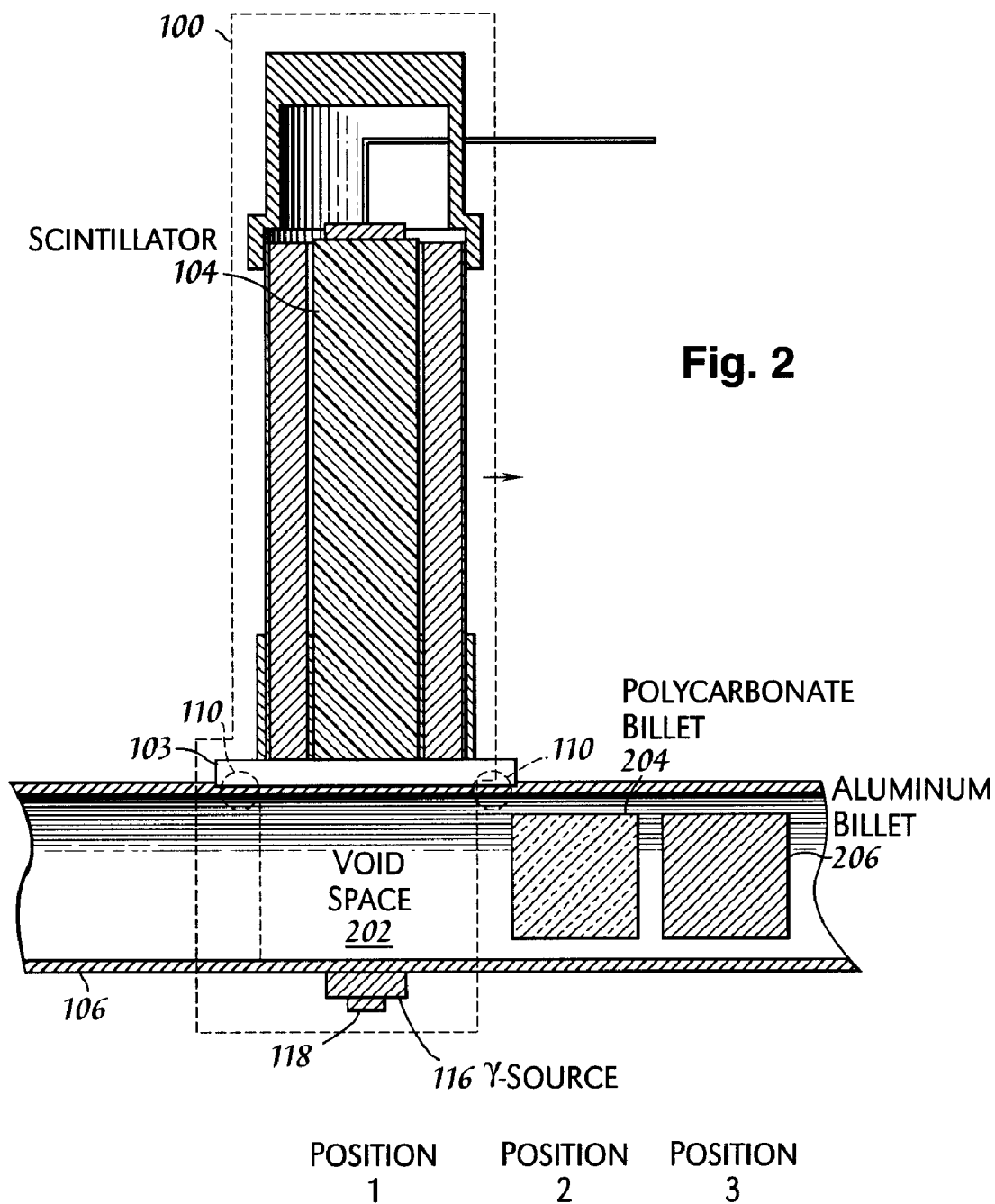

PORTABLE GAMMA APPARATUS FOR CORE ANALYSIS AND METHOD THEREFOR

TECHNICAL FIELD

The present invention relates in general to the determination of porosity in petroleum well cores, and in particular, to the determination of core density using gamma-ray densitometry.

BACKGROUND INFORMATION

The attenuation of gamma (γ) rays from an artificial source can be used to determine the density of a core sample taken from a stratigraphic exploration well. A γ-ray analysis of the core at the wellsite is used in order to make the preliminary selection of portions of the core which are to be further analyzed in a laboratory. Furthermore, preliminary analysis of the core at the drilling site may be useful in guiding the drilling of additional core samples. A system for the wellsite analysis of core samples, for natural γ activity, has been described in U.S. Pat. No. 4,854,163 to Mount, et al. Mount, et al. is directed to an analysis of the natural γ activity of the core sample, which is useful for correlating positions along the core sample with locations within the borehole.

Modern coring technology uses coring techniques in wells which are lined with an inner barrel. These yield core samples which are clad by the barrel. Thus, visual observation of the core quality and of recovery is precluded because the barrel is opaque. (Recovery, the length of core obtained, may be less than the length attempted.) Typically, it is impractical to remove the core from the pipe at the wellsite for such observations. Moreover, barrel-clad core samples are used to obtain core samples in unconsolidated strata. In such strata, the core sample, if not confined by the barrel, would disintegrate into an unstratified mix of the constituent core material, rendering the analysis of the core useless. Such strata are commonly encountered at off-shore wellsites. Therefore, a wellsite analysis system similar to that taught in Mount, et al. may not be usable for the well-site analysis of barrel-liner-clad cores. Thus, in order to access the core within the pipe for analysis, the core sample must be frozen, typically using cryogenic means. The frozen core may then be sectioned for analysis. However, these methods are usually impractical at the wellsite.

Consequently, barrel-clad cores must be transported off site for analysis, which is costly in both time and expense. Or, wellsite analysis relies on simple handheld Geiger counters to preliminarily analyze the cores, a process which is prone to inaccuracy because the Geiger counters are not shielded from background radiation and counts are not energy analyzed Therefore, there is a need in the art for a portable apparatus, and method of using the same, for performing a γ-ray analysis of barrel liner-clad cores.

SUMMARY OF THE INVENTION

The aforementioned needs are addressed by the present invention. Accordingly there is provided, in a first form, an apparatus for core analysis having a carriage operable for supporting a γ-ray detector, wherein the carriage is operable for straddling the core and stably traversing a length thereof. The apparatus also includes a support attached to the carriage operable for mounting a γ-ray source distally of the detector and forming a space therebetween operable for passage of the core.

Additionally, there is provided, in a second form, a method of core analysis including the steps of providing a γ-ray analysis apparatus stably straddling the core and detecting natural γ activity from the core. There is also provided a method of core analysis including the steps of providing a γ-ray analysis apparatus stably straddling the core, and detecting γ-rays emitted from a radionuclide source and passing from the source through the core.

The foregoing has outlined rather broadly the features and technical advantages of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which:

FIG. 2 illustrates a calibration structure used with the apparatus of FIG. 1.

DETAILED DESCRIPTION

A portable γ-ray spectrometer apparatus which may be used for determining the core density and porosity of a core sample within a core barrel liner is provided. A γ-ray detector is mounted on a carriage, or skate, assembly. The carriage assembly engages a portion of the core barrel, and is traversable along the core barrel on rollers which run on an outer surface of the core barrel. A bracket assembly attached to the skate supports an artificial γ-ray source, such that the γ-source is disposed opposite the γ-ray detector and with the core barrel, and the core within, disposed therebetween. γ-rays from the artificial source pass through the core barrel and core sample and then into the detector.

In the following description, numerous specific details are set forth, such as specific γ-source radioisotopes, to provide a thorough understanding of the present invention. However, it will be obvious to those skilled in the art that the present invention may be practiced without such specific details.

Figure 1A:
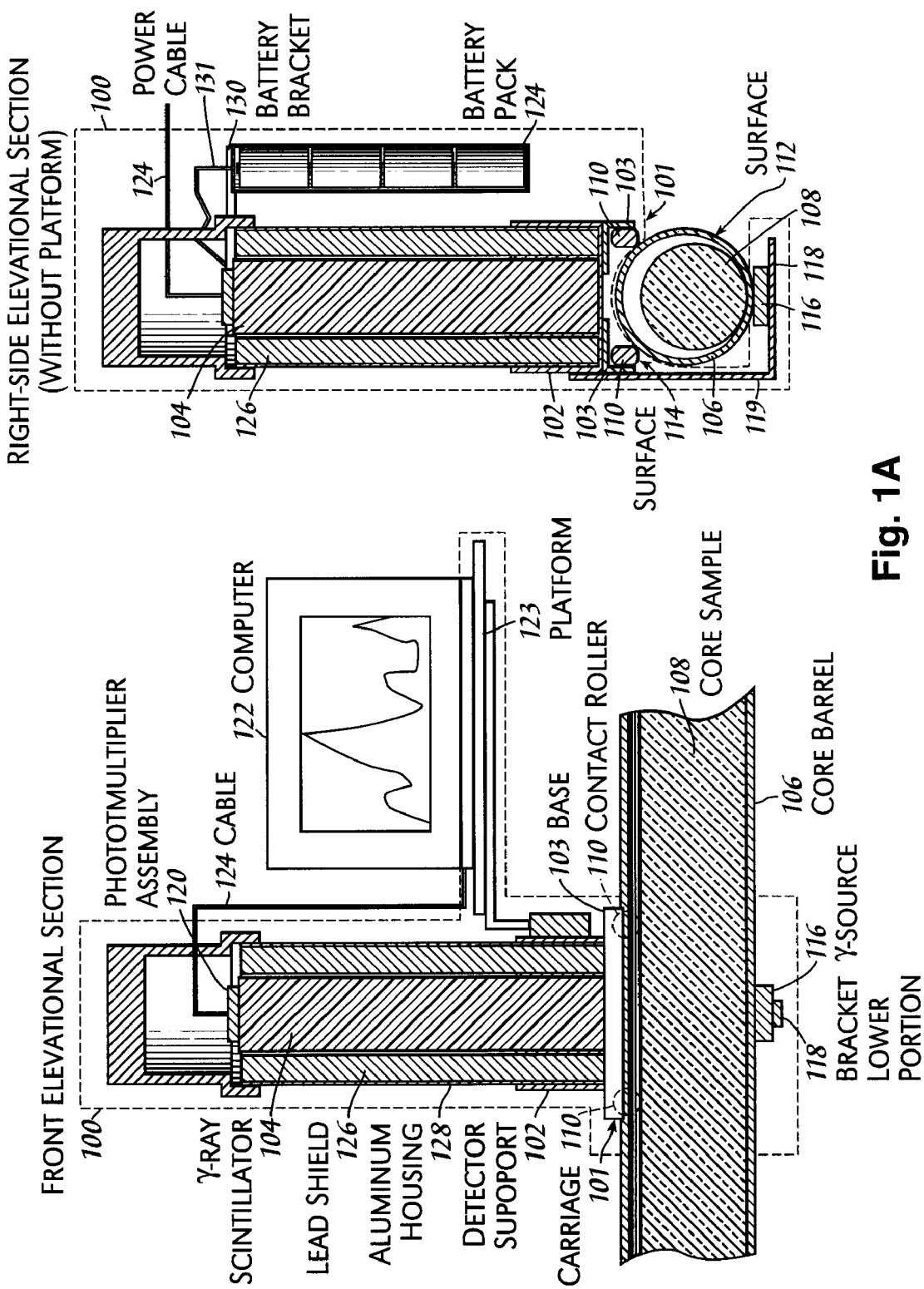
FIG. 1A illustrates an apparatus for determining core quality and recovery in cores within a core barrel liner.

Refer now to the drawings wherein depicted elements are not necessarily shown to scale and wherein like or similar elements are designated by the same reference numeral through the several views. FIG. 1 illustrates, in front elevation section and right-side elevation section, a portable γ-ray apparatus 100 in accordance with the present invention. Carriage 101 supports γ-ray scintillator 104 in proximity to core barrel 106 containing core sample 108. Carriage 101 includes a detector support 102 and a base 103.

Contact rollers 110 are rotatably attached to base 103 of carriage 101. Contact rollers 110 contact an upper portion of an outer surface 112 of core barrel 106, as illustrated in the side elevation in FIG. 1, showing the γ-ray apparatus of the present invention in a right-side elevational section. Contact rollers 110 have a surface 114 having a contour adapted for contacting surface 112 of core barrel 106 in a substantially tangential fashion.

Figure 1B:
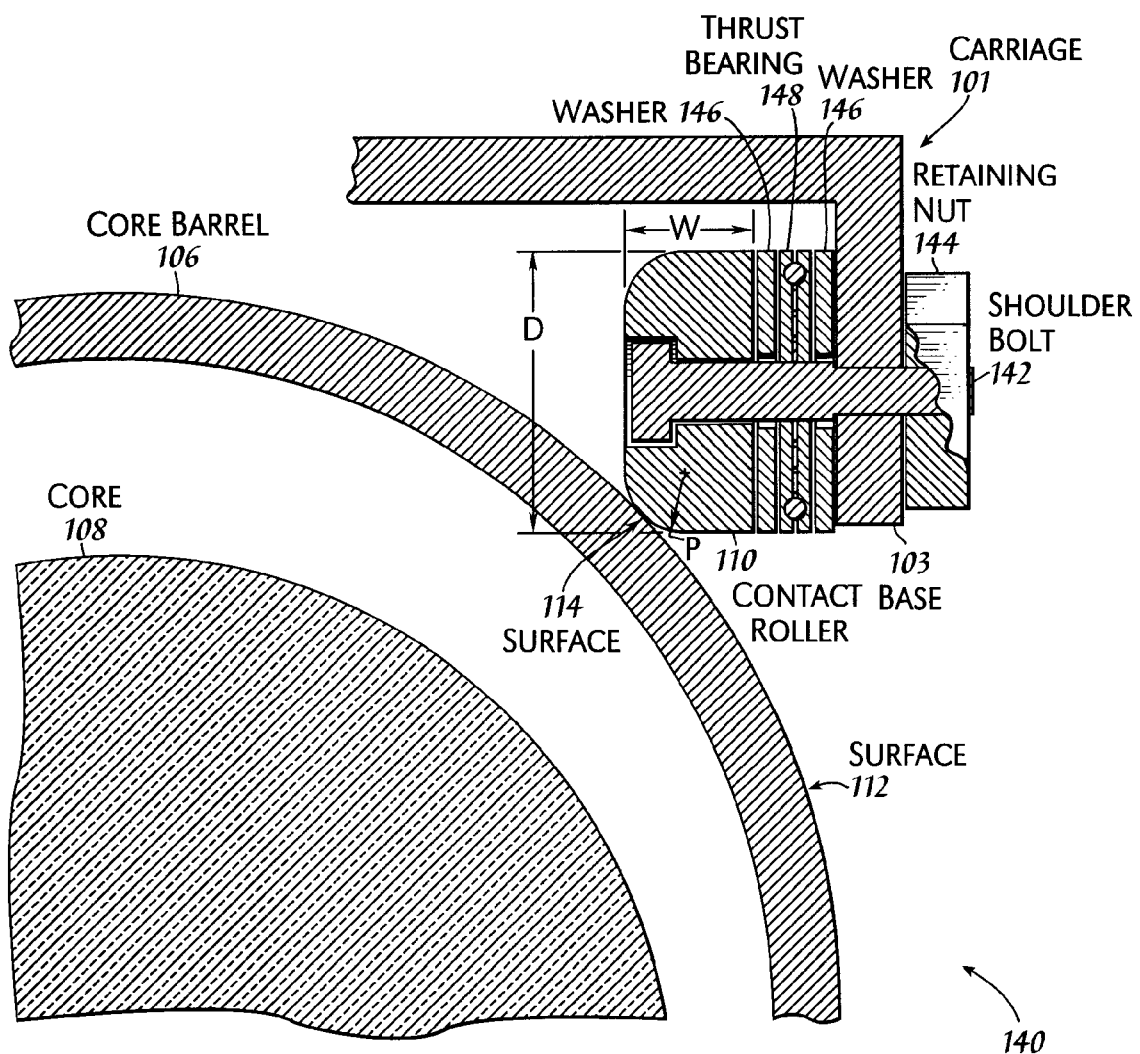
FIG. 1B illustrates a portion of an embodiment of the apparatus of FIG. 1A.

A portion 140 of apparatus 100 illustrating surfaces 114 and 112 in further detail is shown in FIG. 1B. Surface 114 of each contact roller 110 contacts surface 112 of core barrel 106, thereby supporting apparatus 100 and rollers 110 allow it to traverse the length of the core barrel. In an embodiment of the present invention, the contour of surface 114 may be a substantially circular arc, having a radius, ρ. In an exemplary embodiment wherein the contour is a circular arc, the arc may have a radius, ρ of approximately 0.2 inches, in association with a roller having a width, W, of approximately 0.5 inches and a diameter, D, of approximately 1.125 inches. However, it would be understood by an artisan of ordinary skill that alternative embodiments having circular arc contours of other radii would be within the spirit and scope of the present invention.

Figure 1C:
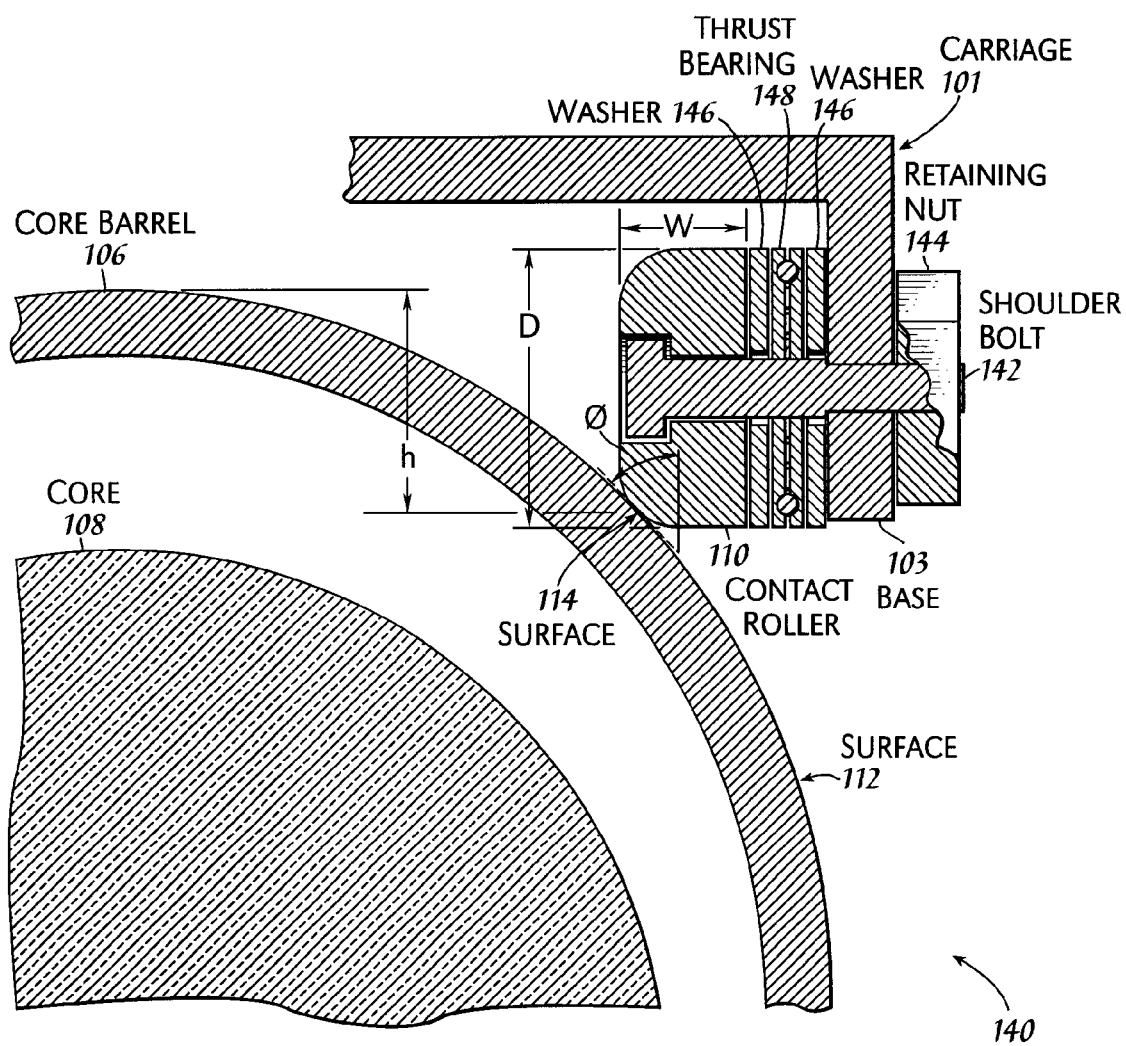
FIG. 1C illustrates a portion of another embodiment of the apparatus of FIG. 1A.

In an alternative embodiment, the contour may be a bevel. Such an embodiment is illustrated in FIG. 1C. Core barrel 106 may be substantially a circular cylinder having a predetermined outer radius a, wherein contact roller 110 has a line of contact with surface 112 substantially parallel to a generatrix of core barrel 106 and located a predetermined distance, h, below a top of core barrel 106. The beveled portion of surface 114 may have an angle, φ, substantially determined by 1−h/a=sinφ.

Each contact roller 110 is attached to base 103 of carriage 101 using a shoulder bolt 142 and a retaining nut 144. Roller 110 is separated from base 103 by a pair of washers 146 and a thrust bearing 148 (shown exploded in FIG. 1B for clarity). In this way, carriage 101 may be stably supported by core barrel 106, mitigating transverse slipping of apparatus 100, and may also be translated along the length of core barrel 106.

Additionally, the support of carriage 101 by core barrel 106 maintains a substantially uniform spacing between γ-source 116 and γ-ray scintillator 104. γ-source 116 is supported by an "L-shaped" bracket having lower portion 118, and upper portion 119 that is attached to carriage 101. Lower portion 118 and upper portion 119 of the L-shaped bracket are more clearly illustrated in the right-side elevational section of γ-ray apparatus 100, FIG. 1. In this way, γ-source 116 is disposed on an opposite side of core barrel 106 from γ-ray scintillator 104. Gamma rays emitted by γ-source 116 in the direction of γ-ray scintillator 104, first pass through core barrel 106 and core sample 108 contained within. The flux of such γ-rays is thereby attenuated by the material of core barrel 106 and core sample 108. By measuring the attenuation for known samples of material within a given core barrel 106, calibration curve can be obtained whereby the density of core sample 108 may be inferred. This will be discussed further in conjunction with FIGS. 2 and 3 below. Gamma source 116 may be $C_s^{137}$. However, other γ-emitting radioisotopes are known in the art, and it would be understood by a practitioner of ordinary skill that such other radioisotopes may be used with the present invention. By maintaining a substantially uniform distance between γ-source 116 and scintillator 104, an improved measurement of the properties of core sample 108 in a well-site environment may be obtained with the present invention.

Additionally, the γ-ray apparatus of the present invention may be used without γ-source 116 to measure the natural γ activity of core sample 108. As previously described, such measurements, for example, be used in correlating positions along core sample 108 with locations within the borehole.

Gamma rays, either from a γ-source 116, or naturally emitted γ radiation from core sample 108 passing to γ-ray scintillator 104, which may be a commercially available NaI scintillator. In an embodiment of the present invention, scintillator 104 may be included in a commercial detector assembly, such as a NanoSpec-2CS™ gamma system manufactured by Oxford Instruments, Inc. Gamma-ray scintillator 104 emits lights in response to the γ radiation, and such light is detected by photomultiplier assembly 120. Photomultiplier assembly 120 generates a signal in response to the emitted scintillation light impinging thereon, which signal is encoded in a serial data format and input to a serial input of computer 122 via cable 124. Photomultiplier signals are interpreted by multichannel analyzer (MCA) software running on computer 122 which may be commercially available MCA software, such as the ASSAYER™ software of Oxford Instruments, Inc., and included in the NanoSpec-2CS system, which software is compatible with the Windows 95™ operating system. Computer 122 may be a commercial "laptop" computer as are well known in the data processing art, running an operating system compatible with the analyzer software. Computer 122 may typically include program storage media and circuitry for storing information well-known in the data processing art, such as disk storage devices including a hard disk and a floppy disk drive.

Photomultiplier assembly 120 may be included in a commercial detector assembly such as the NanoSpec-2CS detector manufactured by Oxford Instruments, Inc. Computer 122, under the control of the multichannel analyzer software, outputs a γ-ray spectrum providing a γ-ray intensity as a function of the energy of the γ-rays, which as noted hereinabove may be the γ-rays emitted from a γ-source 116, or alternatively, naturally occurring γ radiation from core sample 108.

In order to reduce γ-ray backgrounds reaching scintillator 104, γ-ray scintillator 104 is surrounded by lead shield 126. Additionally, aluminum housing 128 surrounds lead shield 126, thereby protecting the soft lead shield, and isolating it from the environment. Electrical power is supplied to photomultiplier assembly 120 by battery pack 129, shown in the right-side elevation in FIG. 1. Battery pack 129 is held in place by battery bracket 130 and electrical power provided to photomultiplier assembly 120 by power cable 131. It would be understood by an artisan of ordinary skill that battery pack 129 includes a number of battery cells of a size and type sufficient to power photomultiplier assembly 120 in accordance with a design thereof. For example, in an embodiment of the present invention using the NanoSpec-2CS™ gamma system manufactured by Oxford Instruments, Inc., battery pack 129 includes four size "D" cells serially connected, each of which provides a voltage of approximately 1.5 volts.

The density of core sample 108 may be determined by measuring the γ-ray signal within a defined energy window, after calibration of the γ-ray apparatus of the present invention, using materials of known density. The materials are formed into a geometry which simulates a core measurement geometry. Such materials may be referred to as "calibration billets." An arrangement of a core barrel and calibration billets which may be suitable for calibrating the γ-ray apparatus of the present invention is illustrated in FIG. 2. At position 1 along core barrel 106, the core barrel 106 is empty, forming a void space 202, such as may be found in a core sample 108 having a missing core interval. At position 2 along core barrel 106, a polycarbonate billet 204 is located, and at position 3 along core barrel 106 an aluminum billet 206 is located.

Source 116 is first used to calibrate the MCA. Calibration of the MCA associates one or more energy channels with a known γ spectrum. Calibration of the MCA is performed using techniques that are known in the γ-ray detection art. In an embodiment of the present invention using a commercial detector assembly, such as the NanoSpec-2CS™ system of Oxford Instruments, Inc., calibration of the MCA may be performed in accordance with procedures provided with the ASSAYER™ software instruction manual.

After calibration of the MCA, the γ-ray source is removed from bracket 118, and a measurement of background radiation is made. The background counts may then be subtracted from the counts made in the presence of γ-source 116 to correct for the presence of the background γ radiation. Source 116 is then replaced, and a number of counts is made for a fixed, pre-selected, time interval. An exemplary count result from such a measurement made with γ apparatus 100 in accordance with the principles of the present invention is illustrated in the graph shown in FIG. 3.

Figure 3:
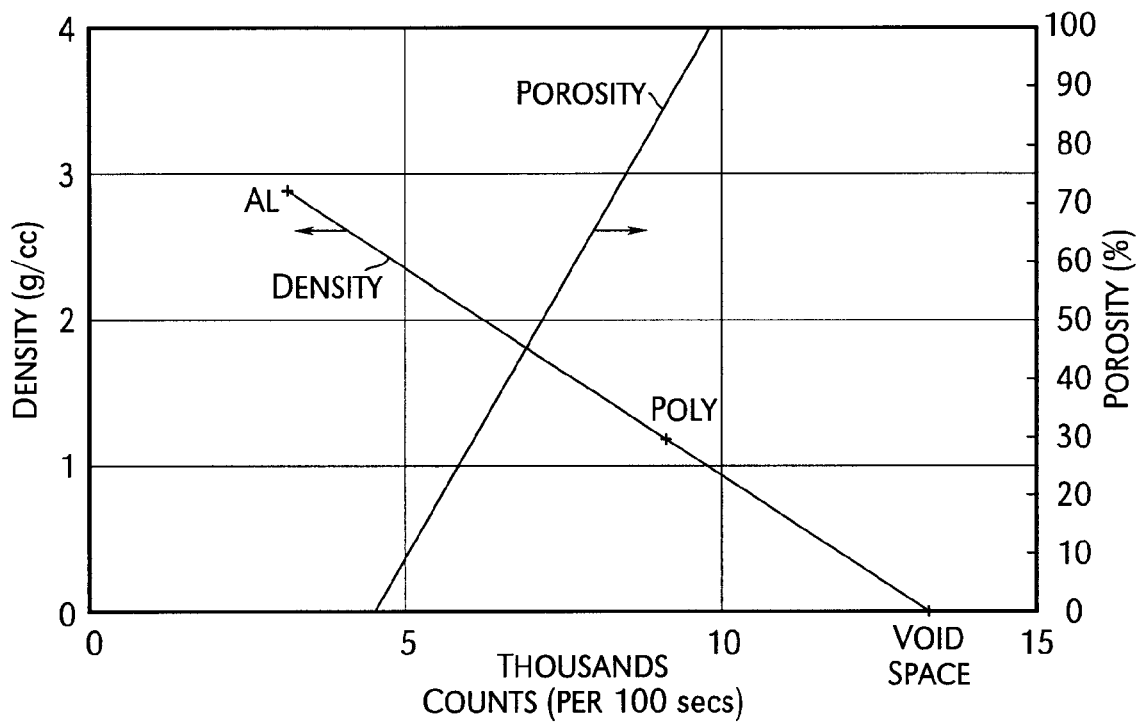
FIG. 3 illustrates an exemplary calibration curve obtained with the calibration structure of FIG. 2.

In FIG. 3, plots of density and porosity versus the number of γ counts is illustrated. The number of counts corresponding to the void spaces indicated by the point labeled "void space," and is plotted having an ordinate corresponding to a density of zero grams per cubic centimeter (g/cc).

Returning to FIG. 2, γ apparatus 100 is positioned over polycarbonate billet 204, at position 2. The measured number of counts is then plotted on the abscissa, in FIG. 3, at a density value on the ordinate corresponding to the density of polycarbonate, approximately 1.2 g/cc.

Apparatus 100 is then positioned over aluminum billet 206 and a γ count over the pre-selected interval of time is made. The number of counts is then plotted on the abscissa in FIG. 3 at the known density of aluminum, approximately 2.7 g/cc. This point is labeled "Al" in FIG. 3. A linear regression of the billet density in counts yields the straight line labeled "Density" in FIG. 3, from which the density of an unknown core sample 108 may be inferred. Such a plot may be referred to as a "calibration transform." Alternatively, the density may be computed by using the equation for the straight line density curve in FIG. 3, Equation (1):

$$\text{Density} = 0.0003 \times \text{counts} + 3.94189 \quad (1)$$

In the exemplary calibration transform of FIG. 3, core barrel 106 was made of aluminum. It would be understood by an artisan of ordinary skill that for other core barrels, a different calibration transform would be obtained and, consequently, a regression equation different from Equation (1) would result. By taking a γ count of an unknown core sample 108 in a core barrel 106 of the same composition used in the calibration, for the pre-selected interval of time, the density of the core sample may be inferred by locating the number of counts on the density curve of FIG. 3, and reading the value of the density at that point on the density scale, which is the "left-hand" scale in FIG. 3 or, alternatively, using a calibration transform equation similar to Equation (1). Gamma measurement data may be stored on a computer readable storage medium, for example, a hard disk or a floppy disk, for subsequent analysis.

From the measurement of the density of the core sample 108, a porosity may be inferred. The porosity of core sample 108 may be related to the density using Equation (2):

$$\text{Porosity } (\%) = \frac{\text{Grain density} - \text{Bulk density}}{\text{Grain density} - \text{Fluid density}} \cdot 100, \quad (2)$$

where the bulk density is the density value obtained from the γ count measurement on core 108, and the calibration transform corresponding to barrel 106. The grain density is the density of the mineral composition from which the core sample is formed, and is initially assumed based on the lithology of the formation from which the sample is taken. The fluid density is the density of any fluids which are trapped in the formation from which the core is taken, and may include a mixture of fluid types, wherein the fluid density is a weighted average calculated from the density of each fluid in the mixture and the fractional amount of the fluid in the mixture. With a value of 2.65 g/cc for the grain density, typical of Gulf Coast and Mid-Continent, or similar, sands, and a value of 1.0 g/cc for the fluid density (i.e. water), and using the density transform in FIG. 3 to determine a density in terms of an observed γ count, the exemplary porosity curve, labeled "Porosity," illustrated in FIG. 3, is obtained. This curve may be used to determine the porosity of core sample 108, in FIG. 1, from the measured γ count. It would be understood by an artisan of ordinary skill, that other porosity curves would be obtained for other, predetermined grain and fluid densities. Density and porosity information may be stored on a computer readable storage medium, such as a hard disk or floppy disk.

It is seen from the curves in FIG. 3, as well as Equations (1) and (2), that as the sample porosity increases, the density correspondingly decreases. Thus, an anomalously high porosity, for example greater than sixty percent (60%), the density is correspondingly anomalously low, less than 1.66 g/cc, for the exemplary curves in FIG. 3. Such a density would indicate a partial recovery or a disrupted or disturbed interval wherein the core sample may be fragmented. If the density approaches 1.00 g/cc, then an inference of missing core would be made. Such information obtained at the wellsite, predicated on a reliable γ bulk density determination, may be useful in order that remedial measures may be expeditiously taken, thereby saving both time and expense.

A portable γ-ray apparatus, which may be used for well-site measurements of core density, and the natural γ spectra of a core sample has been provided. The γ apparatus of the present invention is suitable for well-site measurements on core samples enclosed in a core barrel, without the need for removing the core sample from the barrel. In this way, the γ apparatus of the present invention may be suited to the γ analysis of unconsolidated core samples.

Although the present invention and its advantages have been described in detail, it should be understood that various changes, substitutions and alterations can be made herein without departing from the spirit and scope of the invention as defined by the appended claims.

What is claimed is:

1. An apparatus for core analysis comprising:
   a carriage operable for supporting a γ-ray detector, wherein said carriage is operable for straddling said core and stably traversing a length thereof; and
   a support attached to said carriage operable for mounting a γ-ray source distally of said detector and forming a space therebetween operable for passage of said core.

2. The apparatus of claim 1 wherein said core is contained in a core barrel.

3. The apparatus of claim 1 wherein said carriage comprises:
   a detector support for holding said γ-ray detector;
   a frame attached to said detector support; and
   a plurality of rollers rotatably attached to said frame, wherein said plurality of rollers is adapted for resting on a surface of said core and rolling thereupon.

4. The apparatus of claim 3 wherein each of said plurality of rollers has a surface having a contoured portion, said contoured portion adapted for constraining said carriage from transversely sliding on said core.

5. The apparatus of claim 4 wherein said contoured portion comprises a substantially circular arc.

6. The apparatus of claim 4 wherein said contoured portion comprises a bevel.

7. The apparatus of claim 1 further comprising a shield surrounding said γ-ray detector, said carriage being further operable for supporting said shield.

8. The apparatus of claim 1 further comprising a platform attached to said carriage, said platform being operable for supporting a data processing system.

9. The apparatus of claim 1 wherein said support comprises a bracket having an upper portion attached to said carriage, and a lower portion for supporting said γ-ray source, said lower portion being spaced distally from said γ-ray detector, forming a space therebetween operable for passage of said core.

10. The apparatus of claim 1 wherein said γ-ray detector comprises a scintillator.

11. A method of core analysis comprising the steps of:
providing a γ-ray analysis apparatus stably straddling said core; and
detecting natural γ activity from said core.

12. The method of claim 11 further comprising the step of traversing a length of said core with said apparatus, and repeating said step of detecting natural γ activity from said core.

13. The method of claim 11 wherein said γ-ray analysis apparatus comprises:
a carriage operable for supporting a γ-ray detector, wherein said carriage is operable for straddling said core and stably traversing a length thereof; and
a support attached to said carriage operable for mounting a γ-ray source distally of said detector and forming a space therebetween operable for passage of said core.

14. The method of claim 13 wherein said carriage comprises:
a detector support for holding said γ-ray detector;
a frame attached to said detector support; and
a plurality of rollers rotatably attached to said frame, wherein said plurality of rollers is adapted for resting on a surface of said core and rolling thereupon.

15. The method of claim 14 wherein each of said plurality of rollers has a surface having a contoured portion, said contoured portion adapted for constraining said carriage from transversely slipping on said core.

16. The method of claim 11 further comprising the step of storing γ-ray measurement data on a computer readable storage medium in response to said detecting step.

17. A method of core analysis comprising the steps of:
providing a γ-ray analysis apparatus stably straddling said core; and detecting γ-rays emitted from a radionuclide source and passing from said source through said core.

18. The method of claim 17 further comprising the step of determining a density of said core in response to a number of γ-ray counts obtained in said detecting step.

19. The method of claim 18 further comprising the step of calibrating said apparatus, wherein data output in said calibrating step provides a calibration transform for said step of determining said density of said core.

20. The method of claim 19 wherein said step of calibrating comprises the steps of:
positioning said apparatus over a void space and measuring a first number of γ counts for a preselected time interval;
positioning said apparatus over a first material having a first known density and measuring a second number of γ counts for said preselected time interval;
positioning said apparatus over a second material having a second known density and measuring a third number of γ counts for said preselected time interval; and
generating said calibration transform from a linear regression of said first, second, and third numbers of counts, and said first and second known densities and a null density of said void space.

21. The method of claim 17 wherein said γ-ray analysis apparatus comprises:
a carriage operable for supporting a γ-ray detector, wherein said carriage is operable for straddling said core and stably traversing a length thereof; and
a support attached to said carriage operable for mounting a γ-ray source distally of said detector and forming a space therebetween operable for passage of said core.

22. The method of claim 21 wherein said carriage comprises:
a detector support for holding said γ-ray detector;
a frame attached to said detector support; and
a plurality of rollers rotatably attached to said frame, wherein said plurality of rollers is adapted for resting on a surface of said core and rolling thereupon.

23. The method of claim 22 wherein each of said plurality of rollers has a surface having a contoured portion, said contoured portion adapted for constraining said carriage from transversely slipping on said core.

24. The method of claim 17 further comprising the step of storing γ-ray measurement data on a computer readable storage medium in response to said detecting step.

25. The method of claim 17 further comprising the step of determining a density of said core in response to said step of detecting γ-rays.

26. The method of claim 25 further comprising the step of determining a porosity of said core in response to said step of determining said density.

27. The method of claim 26 further comprising the step of storing density and porosity information on a computer readable storage medium in response to said steps of determining said density and porosity.

* * * * *